United States Patent [19]

Provitt

[11] Patent Number: 5,716,938
[45] Date of Patent: Feb. 10, 1998

[54] MATTRESS FRESHENER AND ROOM DEODORIZER COMPOSITION

[76] Inventor: Robert Darnell Provitt, 7500 Tally Ann Dr., Tallahassee, Fla. 32311

[21] Appl. No.: 686,154

[22] Filed: Jul. 24, 1996

Related U.S. Application Data

[63] Continuation-in-part of Ser. No. 385,031, Feb. 7, 1995, abandoned.

[51] Int. Cl.$^6$ .................................................. A61K 7/46
[52] U.S. Cl. ............................. 512/1; 252/8.6; 512/4
[58] Field of Search ........................ 512/1, 4; 252/8.6

[56] References Cited

U.S. PATENT DOCUMENTS

| | | | |
|---|---|---|---|
| 4,161,449 | 7/1979 | Smith et al. | 252/8.6 |
| 4,304,675 | 12/1981 | Corey et al. | 252/8.6 |
| 4,552,777 | 11/1985 | Dente et al. | 427/393.1 |
| 4,873,000 | 10/1989 | Weller | 252/8.6 |
| 5,246,919 | 9/1993 | King | 512/4 |

*Primary Examiner*—James H. Reamer

[57] ABSTRACT

A powder composition for refreshing a mattress and deodorizing the air in a room where the mattress is located is disclosed. The composition has a fragrance constituent comprising about 8% to 12% by weight, a powder constituent comprising about 8% to 12% by weight, a desiccant constituent comprising about 2% to 8% by weight, and a filler constituent comprising about 68% to 82% by weight. The composition accomplishes both the refreshing of the mattress and the deodorizing of the air in one application, thereby saving labor cost associated therewith in institutional settings such as hospitals, prisons or the like. The fragrance constituent comes in a plurality of scents. The ratio of powder to the fragrance is about between 1:1 to 1.5:1 by weight. The fragrance constituent can be either a solid or liquid material.

10 Claims, No Drawings

MATTRESS FRESHENER AND ROOM DEODORIZER COMPOSITION

This application is a Continuation in Part of application Ser. No. 08/385,031, filed Feb. 7, 1995, now abandoned.

BACKGROUND OF THE INVENTION

1. Field of the Invention

The present invention relates generally to a composition that freshens a mattress and deodorizes room air, and more particularly to a composition which is adapted to freshen not only a mattress, but can also be used on carpets, furniture, automobiles and the like for freshening and deodorizing the air all in one simple step.

2. Description of the Prior Art

Throughout the United states steps are being taken to improve fragrances for stuff furniture, mattress, carpets and the like. The fragrances are designed to eliminate foul odor for rendering deodorized room air.

One such fragrance is disclosed in U.S. Pat. No. 5,246,919 issued to King. In this patent there is disclosed a compound that imparts a fragrance when set out at ambient temperatures or when placed in heated water. This fragrant material is formed mostly of small sodium chloride granules wherein the granules can be molded into a particular shape. Though this product may produce a pleasant fragrance, this product cannot be used on furniture, bedding, or the like. Since King clearly discloses a product which is wet to touch, such a fragrant would stain and possibly ruin the furniture, bedding, or the like. A situation and circumstance which is highly undesirable by the user.

Yet another device is disclosed in U.S. Pat. No. 4,552,777 issued to Dente et al. In this patent, there is discloses a carpet treating composition containing a compound to reduce caking. This compound includes an agglomerating agent in the formula to cause the product to remain in contact with the carpet surface rather than forming a cloud of dust when the carpet is walked on. Though this product may be ideal for use with a carpet or the like, this product contains particles which are large and bulky. These particles, since not in powder form, would be irritating to the user. Thereby providing a fragrant which is not desirable to utilize with furniture, bedding or the like.

Still a further composition is disclosed in U.S. Pat. No. 4,161,449 issued to Smith et al. wherein there is disclosed a powdered carpet composition which is used on a carpet for deodorizing and/or freshening. Smith et al. discloses a composition wherein sodium bicarbonate is a carrier wherein the compound is in the amount of 55–98.99 percent of the total final product. Additionally, Smith et al. also discloses the use of sodium sulfate. The use of sodium sulfate and the large amount of sodium bicarbonate will produce a composition which is grainy. Such a compound is undesirable by a consumer. The use of sodium sulfate would give the illusion of sleeping on sand and not on a mattress. Further still, the grainy substance of Smith et al. is designed to grasp onto the fibers of a carpet for a short period of time, and then is removed via vacuuming. Such a disclosed method clearly teaches that this compound cannot be used on furniture for fear of scratching and ruining the furniture nor can this be used on a mattress since this composition could clearly irritate the consumer.

Accordingly, there exists a need to provide for a composition which can efficiently and successfully be placed on a mattress, in furniture, in an automobile, on a carpet, or the like, for freshening and deodorized a room without irritating the consumer nor causing harm to the home furnishings. No previous efforts have been disclosed which provide the benefits intended with the present invention. Additionally, prior techniques do not suggest the present inventive combination of component elements as disclosed and claimed herein. The present invention achieves its intended purposes, objectives and advantages over the prior art device through a new, useful and unobvious combination of component elements, which is simple to use, with the utilization of a minimum number of functioning parts, at a reasonable cost to manufacture, assemble, test and by employing only readily available material.

SUMMARY OF THE INVENTION

The present invention provides for a composition which is adapted to be used on a mattress for enabling the consumer to refresh and deodorize a room without harming nor irritating the user. The composition of the present invention provides a solution which can be used on any household furnishing. Thereby, providing a composition which is in powder form and which is not irritating to the user.

It has been determined that by preparing a powdered blend of specific particle size, comprising in specific concentrations, a fragrance, a carrier, a desiccant, and a filler, a composition which can easily be used on home furnishing is achieved. Due to the high concentration of filler, the fragrance will not over-power the room, inherently providing a composition which can be left on the home furnishing for an extended period of time.

Specifically, the composition comprises a fragrance ingredient, a desiccant ingredient, a powder ingredient and a filler ingredient. The fragrance can be between 8 to 12% by weight, the desiccant can be from 2 to 8% by weight, the powder can be from 8 to 12% by weight, and the filler can be from 68 to 82% by weight.

The composition is prepared by taking the desired amount of powder and placing the powder in a large mixing bowl. Then, the proper amount of fragrance is added to the powder and an interim mixture is formed and stirred with a mechanical stirrer until the interim mixture is homogenous in texture at room temperature. Then, the desiccant is added to the interim mixture to form a second interim mixture and that second interim mixture is agitated until the second interim mixture achieves a homogenous status at room temperature. Immediately after achieving homogenous status, the filler is added to the second interim mixture to form a final product which is also stirred with the mechanical stirrer until a homogenous state is achieved at room temperature. Thereafter, the final product the transferred to containers via a filling line for shipment to distribution centers. The key to the efficacy of the product is the ratio of the powder to the fragrance. That ratio can vary from a minimum of one part powder to one part fragrance up to a maximum of 1.5 parts powder to 1 part fragrance. Further, the fragrance must always be added to the powder initially for preventing a lumpy and non-uniform composition.

Accordingly, it is the object of the present invention to provide for a composition which can be used for an extended period of time and which can be in direct contact to any home furnishings, such as a mattress, furniture, carpet, or the like for successfully deodorizing and refreshing a room without irritating the consumer.

Another object of the present invention is to provide a deodorizing and refreshing composition which will overcome the deficiencies, drawbacks and shortcomings of prior refreshing compositions and methods thereof.

Yet another object of the present invention is to provide a composition which exhibits excellent performance characteristics regardless of the humidity in the air or the moisture content in the home furnishings, such as a mattress, carpet, or the like.

Still another object of the present invention, to be specifically enumerated herein, is to provide a fragrant composition device in accordance with the preceding objects and which will conform to conventional forms of manufacture, be of simple construction and easy to use so as to provide a device that would be economically feasible, long lasting and relatively trouble free in operation.

Although there have been many inventions related to fragrant compounds, none of the inventions have become sufficiently compact, low cost, and reliable enough to become commonly used. The present invention meets the requirements of the simplified design, compact size, low initial cost, low operating cost, ease of installation and maintainability, and minimal amount of training to successfully employ the invention.

The foregoing has outlined some of the more pertinent objects of the invention. These objects should be construed to be merely illustrative of some of the more prominent features and application of the intended invention. Many other beneficial results can be obtained by applying the disclosed invention in a different manner or modifying the invention within the scope of the disclosure. Accordingly, a fuller understanding of the invention may be had by referring to the detailed description of the preferred embodiments in addition to the scope of the invention defined by the claims taken in conjunction with the accompanying drawings.

DESCRIPTION OF THE PREFERRED EMBODIMENTS

The present invention provides a composition which can be left on home furnishings for an extended period of time, i.e. two weeks, for refreshing and deodorizing the room. This composition of the present invention is designed and formulated to be readily used by the consumer. The product will not irritate the user upon contact with the composition.

For enabling a composition to be used on home furnishing without damaging nor harming the furniture, the composition will be in powder form. Thereby, providing the particles to be fine or very fine in size.

The composition of the present invention comprises a filler ingredient, a fragrance ingredient, a desiccant ingredient, and a powder ingredient. The composition must have a specific concentration so as to provide for a product which is not overbearing and which will enable the freshener to remain on a particular object for an extended period of time.

The primary ingredient in this composition is a filler. The filler will dilute the fragrance ingredient. This will render a fragrance which is not overbearing to the consumer. Since the composition may be in contact with the user, for example if the product is used on a mattress, the filler must be non-toxic, inert, low density, and biodegradable. Fillers include talcum, starches, silica powders and the like. Preferably, talc is utilized due to its low cost and accessibility.

The fragrance is conventional and may comprise natural material, synthetic aromatic agents, or a combination thereof to provide for a fragrance which can be in a liquid form or a solid form. It is noted that Ocean Breeze scent, Honeysuckle Flower scent, Fresh and Clean and Hibiscus scent have been utilized to produce excellent results. Other scents and fragrances which are commercially available may also be employed.

A non-dissolvable powder is used to absorb moisture and to allow the composition to be maintained in powder form. The powder will prevent the composition from being wet and/or gummy so as to render a product which will not damage or ruin home furnishings, such as a matters, sofa, carpet, or the like. Powders which can be used include magnesium carbonate or magnesium silicate. Preferably magnesium carbonate is utilized.

The composition of the present invention also includes a desiccant. The use of a desiccant is to absorb odor to inherently deodorize the area. Preferably, sodium bicarbonate is used as the desiccant.

The concentration of the fragrance can be between 8 to 12% by weight, the desiccant can be from 2 to 8% by weight, the powder can be from 8 to 12% by weight, and the filler can be from 68 to 82% by weight.

The composition which is powdered in its final form must be prepared in a sequential manner for preventing a final product which is lumpy and non-uniform. The first step in preparing the composition is to place the proper amount of powder, such as magnesium carbonate, in a large bowl. Then a proper amount of fragrance is added and stirred with a mechanical stirrer to form an interim product. This interim product is stirred until it is a homogenous powdered mixture at room temperature. By adding the fragrance to the powder will provide a final product which is dry and uniform in structure. The fragrance must always be added to the powder first in order to prevent a lumpy and non-uniform composition.

The desiccant, such as sodium bicarbonate, is added to the interim mixture to form a second interim mixture. The second interim mixture which contains the fragrance and the powder and the desiccant is agitated at room temperature with the mechanical stirring device until the second interim mixture has achieved a homogenous status. Immediately upon achieving a homogeneous status, the filler, such as talc, is added to the second interim mixture to form a final product by stirring with the mechanical stirrer until the final product achieves a homogeneous status at room temperature. Once the final product has achieved a homogeneous status, the composition can be placed in a container, package or the like, for enabling the product to be in condition for shipping to retail stores or the like.

The effectiveness of formulation made in accordance with the teaching of the present invention is illustrated by the following example. In the example provided, the parts are given by weight.

EXAMPLE

The following example is a typical product which has been utilized to produce favorable and successful results.

| Compound | Substance | Concentration |
| --- | --- | --- |
| Filler | Talc | 74% |
| Powder | Magnesium Carbonate | 10% |
| Fragrance | Ocean Breeze | 10% |
| Desiccant | Sodium Bicarbonate | 6% |

The above identified composition was prepared by first mixing the magnesium carbonate with the fragrance. Once an homogeneous mixture was achieved, the sodium bicarbonate was mixed into the solution until a homogeneous mixture was achieved. The talc was mixed into the solution until a homogeneous mixture was obtained. The mixing process occurred at room temperature.

The product was sprinkled directly on the mattress. The bed was made by placing a fitted sheet on the mattress. It was observed that the product provided a pleasant odor and did not cause irritation. Due to the fine size of the particles of the product, the user was did not feel its presence.

After a week, the sheets were removed, washed and replaced on the mattress. The refresher maintained its aroma for an additional week. Additionally, it was observed that the product not only absorb odor, but also prevented a wet feeling on the bed. No staining occurred on the mattress.

The same product was used on a carpet. The carpet was first vacuumed and the product was brushed into the carpet. It was observed that the room smelled refreshed. This aroma lasted until the next vacuuming. No staining occurred on the carpet.

A generous amount of the product was also place under the cushion of a sofa. The pleasant fragrance last at least two weeks. No staining occurred on the sofa.

It is seen that this composition will successfully produce a pleasant fragrance for the consumer by providing a product which can be left on a particular product. This product can come into contact with the consumer without irritating the user.

It is noted that the ratio of powder, such as magnesium carbonate to fragrances can range from a minimum of one part powder to one part of fragrance to a maximum of 1.5 parts of powder to one part of fragrance. This will still produce a composition which will successfully refresh and deodorize a room.

Although there are many products available that will refresh and/or deodorize the air in a room, there does not exist a product that allows a person to perform both functions with one application of a single product in one step. This is extremely important when it comes to the institutional and the commercial applications of the product. For example, in military barracks settings, hospital settings, and hotel/motel settings this activity is done with very high labor cost content. The ability of one product to perform two functions saves not just the product cost, but also saves the labor to apply the product. This invention will result in a large reduction of the unit labor cost to maintain a bed whether it is in a hospital, military, or commercial setting.

While the invention has been particularly shown and described with reference to an embodiment thereof, it will be understood by those skilled in the art that various changes in form and detail may be made without departing from the spirit and scope of the invention.

I claim:

1. A powder composition for refreshing and deodorizing a room consisting essentially of:

a fragrance comprising about 8% to 12% by weight for refreshing the room;

a powder comprising about 8% to 12% by weight for preventing a wet and gummy substance;

said powder is selected from the group consisting of magnesium carbonate, magnesium silicate, and a blend thereof;

a desiccant for absorbing the odors entrained in the room air comprising about 2% to 8% by weight;

said desiccant is sodium bicarbonate;

a filler comprising about 68% to 82% by weight for diluting said fragrance to remain in aromatic coupling with the powder;

said filler is selected from the group consisting of talc, starches, silica powders, and a blend thereof; and said fragrance, said powder, said desiccant, and said filler for a compound, and said compound is formed from very fine particles to provide for said compound to be in a powder form.

2. A powder compound as in claim 1 wherein the ratio of powder to fragrance is about between 1:1 to 1.5:1, by weight.

3. A powder compound as in claim 1 wherein said fragrance is a liquid.

4. A powder compound as in claim 1 wherein the fragrance is a solid.

5. A powder compound as in claim 1 wherein said filler is 74%, by weight, said powder is 10%, by weight, said fragrance is 10%, by weight, and said desiccant is 6% by weight.

6. A method of formulating a room freshener and deodorizer powder compound comprising the steps of:

mixing a fragrance of about between 10% by weight with a powder comprising about 8 to 12% by weight at room temperature;

said powder is selected from the group consisting of magnesium carbonate, magnesium silicate, and a blend thereof;

using a stirrer to obtain a uniform mixture and produce an interim product;

adding a desiccant comprising 2 to 8% and a filler comprising 68 to 82%;

said desiccant is sodium bicarbonate;

said filler is selected from the group consisting of talc, starches, silica powders, and a blend thereof; and using a stirrer at room temperature to produce a homogeneous final mixture.

7. A method as in claim 6 wherein the ratio of powder to fragrance is about between 1:1 to 1.5:1, by weight.

8. A method as in claim 6 wherein said fragrance is a liquid.

9. A method as in claim 6 wherein the fragrance is a solid.

10. A method as in claim 6 wherein said filler is 74%, by weight, said powder is 10%, by weight, said fragrance is 10%, by weight, and said desiccant is 6% by weight.

* * * * *